(12) United States Patent
Prevost et al.

(10) Patent No.: US 9,271,844 B2
(45) Date of Patent: Mar. 1, 2016

(54) EXPANDABLE SPINAL IMPLANT SYSTEM AND METHOD

(71) Applicant: Warsaw Orthopedic, Inc, Warsaw, IN (US)

(72) Inventors: Julien J. Prevost, Memphis, TN (US); Charles Britt, Southaven, MS (US); Kyle Hess, Memphis, TN (US); David R. Kaes, Toms River, NJ (US); Kelly W. Schlachter, Mason, TN (US); Guobao Wei, Milltown, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 210 days.

(21) Appl. No.: 13/801,170

(22) Filed: Mar. 13, 2013

(65) Prior Publication Data

US 2014/0277480 A1    Sep. 18, 2014

(51) Int. Cl.
*A61F 2/44*  (2006.01)
*A61F 2/30*  (2006.01)
*A61F 2/28*  (2006.01)

(52) U.S. Cl.
CPC ............... *A61F 2/4455* (2013.01); *A61F 2/44* (2013.01); *A61F 2002/2835* (2013.01); *A61F 2002/30062* (2013.01); *A61F 2002/30092* (2013.01); *A61F 2002/30235* (2013.01); *A61F 2002/30405* (2013.01); *A61F 2002/30556* (2013.01); *A61F 2002/30579* (2013.01); *A61F 2002/30601* (2013.01); *A61F 2002/30733* (2013.01); *A61F 2002/30841* (2013.01); *A61F 2002/4475* (2013.01)

(58) Field of Classification Search
USPC ............................. 623/17.11–17.16
See application file for complete search history.

(56) References Cited

U.S. PATENT DOCUMENTS

| | | | | |
|---|---|---|---|---|
| 5,702,449 | A * | 12/1997 | McKay | 623/17.16 |
| 8,231,681 | B2 | 7/2012 | Castleman et al. | |
| 8,328,871 | B2 * | 12/2012 | Capote et al. | 623/17.16 |
| 2002/0022887 | A1 | 2/2002 | Huene | |
| 2002/0116066 | A1 | 8/2002 | Chauvin et al. | |
| 2009/0112325 | A1 * | 4/2009 | Refai et al. | 623/17.16 |
| 2009/0138083 | A1 | 5/2009 | Biyani | |
| 2009/0164018 | A1 * | 6/2009 | Sommerich et al. | 623/17.16 |
| 2009/0187248 | A1 * | 7/2009 | Dewey et al. | 623/17.16 |
| 2009/0281625 | A1 | 11/2009 | Enayati | |
| 2010/0274357 | A1 * | 10/2010 | Miller et al. | 623/17.16 |

* cited by examiner

*Primary Examiner* — Sameh Boles
(74) *Attorney, Agent, or Firm* — Sorell Lenna & Schmidt LLP (57) ABSTRACT

A spinal implant comprises a first member including a wall that defines a first cavity and a second member including a wall defining a second cavity. At least one first expandable bone graft is disposable within the second cavity. The second member is axially translatable relative to the first member between a first configuration and a second, expanded configuration such that at least a portion of the at least one first graft is disposed within the first cavity and the first cavity includes a substantially void portion. At least one second bone graft has a selective configuration and dimension for disposal within the substantially void portion. Systems and methods are disclosed.

13 Claims, 5 Drawing Sheets

EXPANDABLE SPINAL IMPLANT SYSTEM AND METHOD

TECHNICAL FIELD

The present disclosure generally relates to medical devices for the treatment of musculoskeletal disorders, and more particularly to a surgical system that includes an expandable spinal implant and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. This disclosure describes an improvement over these prior art technologies.

SUMMARY

In one embodiment, a spinal implant is provided. The spinal implant comprises a first member including a wall that defines a first cavity. A second member extends between a first end and a second end and defines a longitudinal axis. The second member includes a wall defining a second cavity. At least one first expandable bone graft is disposable within the second cavity. The second member is disposable within the first cavity and axially translatable relative to the first member between a first configuration and a second, expanded configuration such that at least a portion of the at least one first graft is disposed within the first cavity and the first cavity includes a substantially void portion. At least one second bone graft has a selective configuration and dimension for disposal within the substantially void portion. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

The exemplary embodiments of the surgical system and related methods of use disclosed are discussed in terms of medical devices for the treatment of musculoskeletal disorders and more particularly, in terms of a surgical system that includes an expandable spinal implant and a method for treating a spine. In one embodiment, the system comprises a spinal implant including an interbody fusion device. In one embodiment, the system comprises a spinal implant including an expandable cage. In one embodiment, the spinal implant includes expandable pre-shaped demineralized allograft. In one embodiment, the system comprises a spinal implant including an in vivo expandable corpectomy cage. In some embodiments, the system includes bone graft, such as, for example, specially formed and cut versions of an allograft material configured to fit and conform to an interior space of a corpectomy cage. In other embodiments, the bone graft may include other materials, including but not limited to: shaped xenograft material; shaped biological materials; shaped/expandable polymer-bone composites; allograft material; and combinations thereof.

In one embodiment, the system comprises an expandable spinal implant that is employed with a method that includes the steps of pre-packing and post-packing the spinal implant with bone graft, such as, for example, 100% demineralized cortical and cancellous allograft. In one embodiment, the method includes the steps of expanding the spinal implant. In one embodiment, the method includes the steps of rehydratation of the allograft in-vivo, such that the allograft expands to fill any void(s) created by the expansion of the spinal implant.

In one embodiment, one or all of the components of the surgical system are disposable, peel-pack, pre-packed sterile devices used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

In some embodiments, the system of the present disclosure comprises a spinal implant that includes bone graft, for example, osteograft. As used in the specification and including the appended claims of the present disclosure, the term "bone graft" includes materials that may include both synthetic and natural bone. In some embodiments, natural bone may be taken from the graft recipient, for example, autograft, or may be taken from another source, for example, allograft, such as a cadaver, or can be xenograft, for example, bovine.

In some embodiments, osteoconduction and osteoinduction both contribute to bone formation. Osteoconductivity provides a structural framework or microscopic and macroscopic scaffolding for cells and cellular materials that are involved in bone formation, for example, osteoclasts, osteoblasts, vasculature and mesenchymal cells. Osteoinductive material stimulates differentiation of host mesenchymal cells into chondroblasts and osteoblasts. Natural bone allograft materials can comprise either cortical or cancellous bone. In some embodiments, allografts can comprise mammalian cadaver bone treated to remove all soft tissue, including marrow and blood, and then textured to form a multiplicity of holes of selected size, spacing, and depth. In some embodiments, the textured bone section can be immersed and demineralized, for example, in a dilute acid bath.

In some embodiments, allografts are formed of organic bone matrix with perforations that extend from one surface, through the matrix, to the other surface to provide continuous channels between opposite surfaces. In some embodiments, partially-demineralized cortical bone constructs may be surface-demineralized to prepare the graft to be soaked in bone growth-promoting substances such as bone morphogenetic protein (BMP).

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there is illustrated components of a surgical system, such as, for example, a spinal implant system 10 in accordance with the principles of the present disclosure.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elastoplastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. In some embodiments, spinal implant system 10 may be employed with surgical procedures, such as, for example, corpectomy and discectomy, which include fusion and/or fixation treatments that employ implants, in accordance with the principles of the present disclosure, to restore the mechanical support function of vertebrae.

Figure 1:
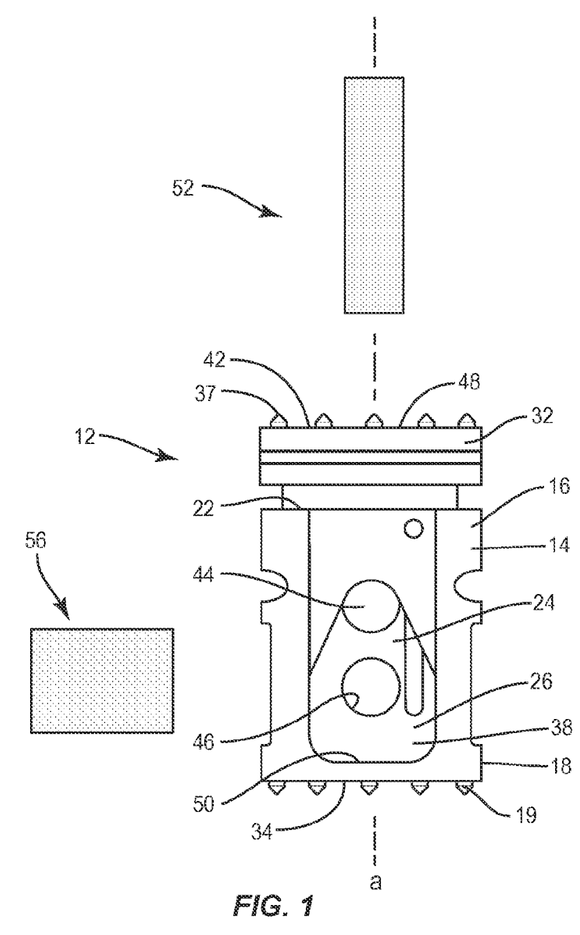
FIG. 1 is a plan view of components of one embodiment of a surgical system in accordance with the principles of the present disclosure.

Spinal implant system 10 includes an implant, such as, for example, a corpectomy cage 12 having a member, such as, for example, an outer body 14. Body 14 has a tubular configuration. Body 14 is substantially cylindrical and extends between an end 16 and an end 18 and defines a longitudinal axis a. End 16 defines a substantially planar surface. End 18 defines a substantially planar surface including fixation elements, such as, for example, spikes 19 configured to engage vertebral tissue. In some embodiments, end 16 and/or end 18 can include a surface that may be rough, textured, porous, semi-porous, dimpled and/or polished such that it facilitates engagement with tissue. In some embodiments, both or only one of ends 16, 18 may engage tissue to provide treatment. In some embodiments, the vertebral tissue may include intervertebral tissue, endplate surfaces and/or cortical bone.

Body 14 includes a tubular wall 20 that includes an inner surface 22. Surface 22 defines an axial cavity 24 extending between ends 16, 18. In some embodiments, wall 20 defines a cylindrical cross-section of cavity 24. In some embodiments, the cross-section geometry of cavity 24 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surface 22 is smooth or even. In some embodiments, surface 22 may be rough, textured, porous, semi-porous, dimpled and/or polished.

Wall 20 defines a lateral opening 26 that communicates with cavity 24. Opening 26 is configured to provide access to cavity 24. In one embodiment, opening 26 facilitates delivery and/or introduction of an agent and/or an implant, such as, for example, bone graft and/or other materials, as described herein, into cavity 24. In some embodiments, opening 26 may have various configurations, such as, for example, circular, oval, oblong, triangular, rectangular, polygonal, planar side(s), arcuate side(s), irregular, uniform, non-uniform, offset, staggered, variable, U-shape, kidney bean shape and/or multiple openings.

Wall 20 defines openings 28 configured to facilitate delivery and/or introduction of an agent, bone graft and/or other materials, as described herein, into cavity 24, for employment in a fixation or fusion treatment used for example, in connection with a corpectomy. In one embodiment, the agent may include therapeutic polynucleotides or polypeptides and bone growth promoting material, which can be packed or otherwise disposed on or about the surfaces of the components of spinal implant system 10, including cage 12. The agent may also include biologically active agents, for example, biologically active agents coated onto the exterior and/or interior of cage 12 and/or applied thereto for gradual release such as by blending in a bioresorbable polymer that releases the biologically active agent or agents in an appropriate time dependent fashion as the polymer degrades within the patient. Suitable biologically active agents include, for example, BMP and cytokines. In some embodiments, openings 28 may have various configurations, such as, for example, those described herein.

The planar surface of end 16 defines an opening 30 that communicates with cavity 24. Opening 30 has a rectangular configuration and is configured to provide access to cavity 24. Opening 30 facilitates disposal of a member, such as, for example, inner body 32 with cavity 24, as described herein. The planar surface of end 18 defines an opening 34 that communicates with cavity 24. Opening 34 has a rectangular configuration and is configured to provide access to cavity 24. In some embodiments, opening 30 and/or opening 34 may have various configurations, such as, for example, those described herein.

Body 32 has a tubular configuration. Body 32 is substantially rectangular and extends between an end 36 and an end 38 and extends along longitudinal axis a. End 36 defines a substantially planar surface including fixation elements, such as, for example, spikes 37 configured to engage vertebral tissue. End 38 defines a substantially planar surface. In some embodiments, end 36 can include a surface that may be rough, textured, porous, semi-porous, dimpled and/or polished such that it facilitates engagement with tissue. In other embodiments, body 32 may have a variety of alternative cross-sectional configurations including, but not limited to: round; oval; "U" or "C" shaped; and combinations thereof.

Body 32 includes a tubular wall 40. Wall 40 includes an inner surface 42 that defines an axial cavity 44 extending between ends 36, 38. In some embodiments, wall 40 defines a rectangular cross-section of cavity 44. In some embodiments, the cross-section geometry of cavity 44 may have various configurations, such as, for example, those described herein. In some embodiments, surface 42 is smooth or even. In some embodiments, surface 42 may be rough, textured, porous, semi-porous, dimpled and/or polished.

Wall 40 defines lateral openings 46 that communicate with cavity 44. Openings 46 are configured to provide access to cavity 44. In one embodiment, openings 46 facilitate delivery and/or introduction of an agent, as described herein, into cavity 44. In some embodiments, openings 46 may have various configurations, such as, for example, those described herein.

The planar surface of end 36 defines an opening 48 that communicates with cavity 44. Opening 48 has a circular configuration and is configured to provide access to cavity 44. In one embodiment, opening 48 facilitates delivery and/or introduction of an agent and/or an implant, such as, for example, bone graft and/or other materials, as described herein, with cavity 44. The planar surface of end 38 defines an opening 50 that communicates with cavity 44 and cavity 24. Opening 50 has a rectangular configuration and is configured to provide access to cavity 44 and cavity 24. In some embodiments, opening 48 and/or opening 50 may have various configurations, such as, for example, those described herein.

Spinal implant system 10 includes a bone graft implant, such as, for example, an expandable insert 52. Insert 52 is configured for disposal within cavity 44. Insert 52 comprises expandable bone graft material, see, for example, the implants and materials described in commonly owned US Patent Application Publication No. 2008/0091270 to Miller et al., the entire contents of which being hereby incorporated by referenced herein. For example, in one embodiment, insert 52 is expandable from a first configuration to a second, expanded configuration upon exposure to liquid in vivo. In some embodiments, such liquid includes body fluids of a patient. In some embodiments, insert 52 includes demineralized cancellous bone particles and demineralized cortical bone particles such that insert 52 is expandable upon rehydration in vivo. In some embodiments, insert 52 comprises bone graft, such as, for example, those materials described herein.

Figure 4:
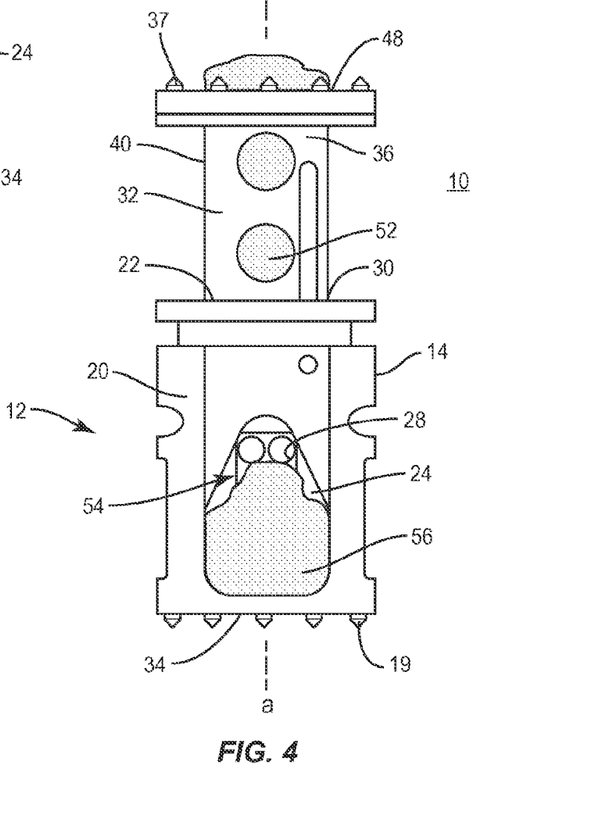
FIG. 4 is a plan view of the components shown in FIG. 1.

In some embodiments, insert 52 is expandable within cavity 44 and/or through opening 50 into cavity 24. In some embodiments, insert 52 is expandable in one or both axial directions along axis a, and/or in a transverse direction, including angular orientations and perpendicular relative to axis a. In some embodiments, bodies 14, 32 are expandable independent of insert 52. In some embodiments, insert 52 is expandable between a first, non-expanded configuration, as shown in FIG. 1, and a second, expanded configuration, as shown in FIG. 4, such that insert 52 engages inner surface 22. Inner surface 22 includes an expansion limit for lateral expansion of insert 52.

Figure 16:
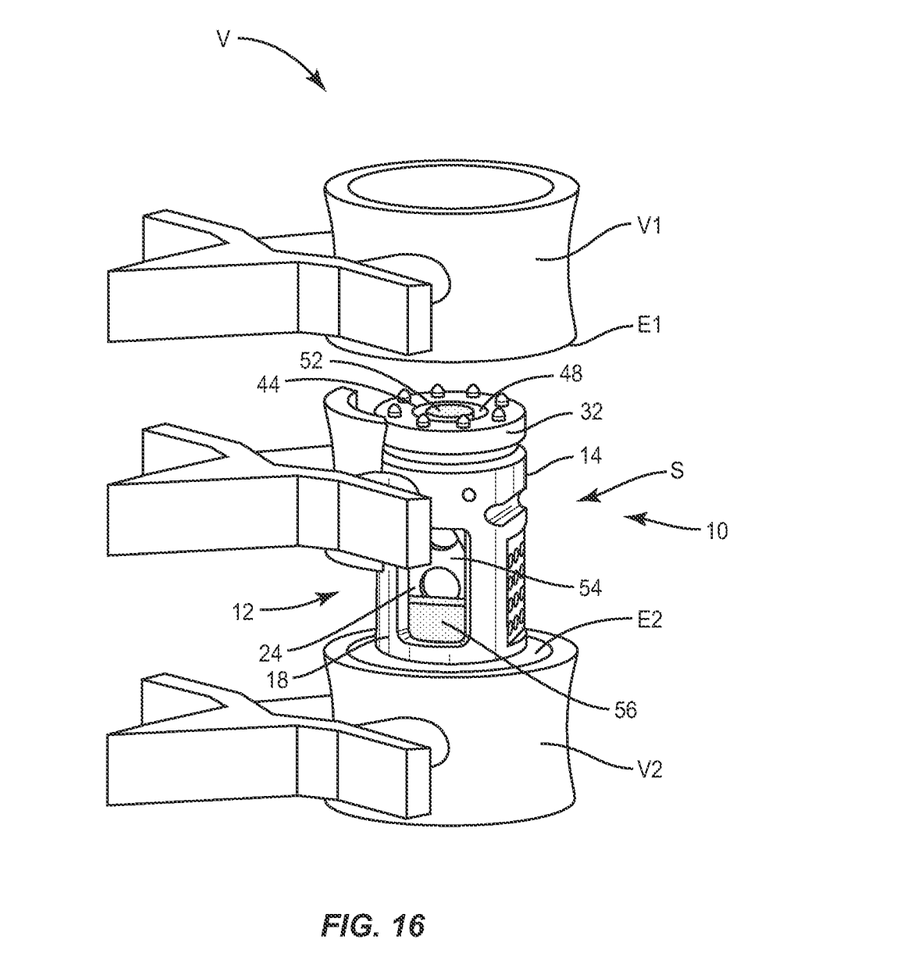
FIG. 16 is a perspective view of components of one embodiment of a surgical system in accordance with the principles of the present disclosure disposed with vertebrae.
Figure 17:
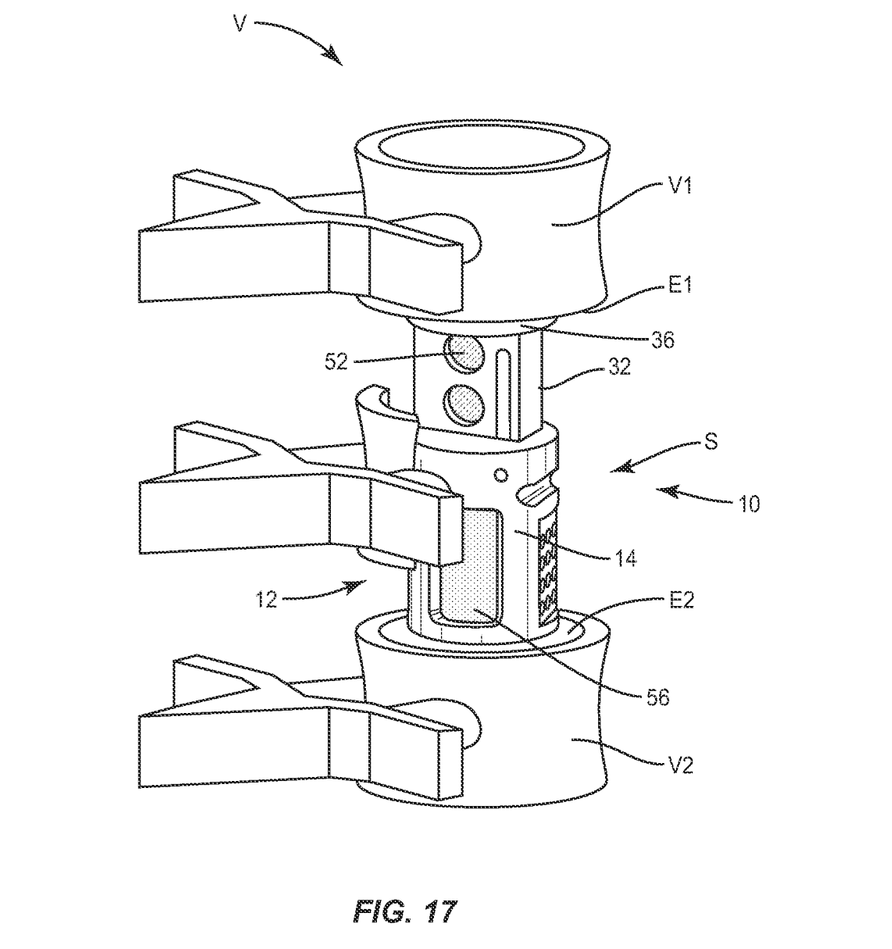
FIG. 17 is a perspective view of the components shown in FIG. 16 disposed with vertebrae.

Cage 12 is selectively movable between a first configuration, such as, for example, as shown in FIG. 1, and a second configuration, such as, for example, as shown in FIG. 4, to restore vertebral spacing and provide distraction and/or restore mechanical support function of vertebrae. In some embodiments, opening 30 facilitates axial translation of body 32 relative to body 14 for selective expansion and/or contraction of bodies 14, 32 between a collapsed and/or nested configuration, as shown in FIG. 16, and an expanded configuration, as shown in FIG. 17. In some embodiments, cage 12 is disposed in a collapsed, telescopic configuration for delivery and implantation adjacent a surgical site and bodies 14, 32 are expanded in vivo. In some embodiments, cage 12 and/or the bone graft inserts described herein can be expanded prior to implantation adjacent a surgical site. In some embodiments, cage 12 can be disposed to engage adjacent vertebral soft tissue and bone surfaces to restore height and provide support in place of removed vertebrae and/or intervertebral tissue.

In one embodiment, expansion and/or contraction of cage 12 is facilitated by engagement of respective helical gear surfaces of bodies 14, 32 such that relative rotation of bodies 14, 32 causes axial translation of body 32 relative to body 14. In one embodiment, expansion and/or contraction of cage 12 is facilitated by engagement of a tool with one of bodies 14, 32 to cause axial translation of body 32 relative to body 14. In one embodiment, expansion and/or contraction of cage 12 is facilitated by free hand manipulation of bodies 14, 32 to cause axial translation of body 32 relative to body 14. In one embodiment, expansion and/or contraction of cage 12 is facilitated by engagement of respective pinion gear and rack surfaces of bodies 14, 32 to cause axial translation of body 32 relative to body 14. In some embodiments, expansion and/or contraction of cage 12 is facilitated by various configurations, such as, for example, mechanical, pneumatic and/or hydraulic components disposed with the surfaces of cage 12, for example, disposed within cavity 24. In some embodiments, cage 12 is configured for continuous expansion, which includes incremental expansion. In some embodiments, incremental expansion may include discrete increments of a particular linear dimension. In some embodiments, the increments of linear dimension may include a range of approximately 0.1-1.0 mm.

Figure 2:
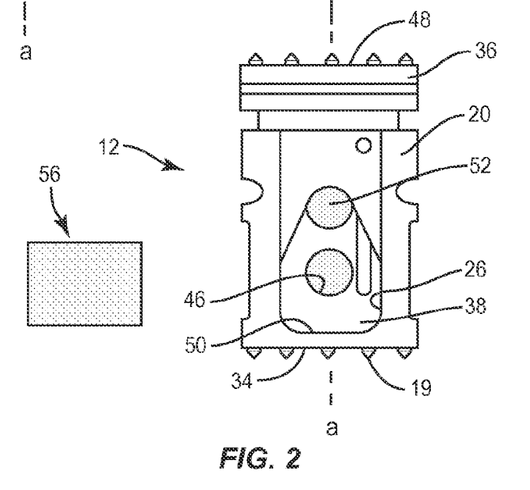
FIG. 2 is a plan view of the components shown in FIG. 1.
Figure 3:
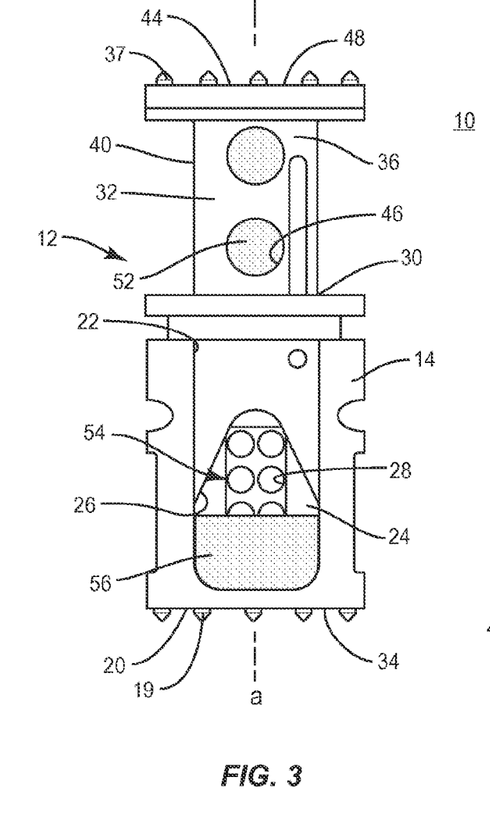
FIG. 3 is a plan view of the components shown in FIG. 1.

Insert 52 is introduced through opening 48, as shown in FIG. 1, and disposed within cavity 44 and body 32 is disposed within cavity 24, as shown in FIG. 2. Body 32 is axially translatable relative to body 14 for selective expansion and/or contraction between a collapsed and/or nested configuration, as shown in FIG. 2, and an expanded configuration, as shown in FIG. 3. Bodies 14, 32 are expanded such that body 32 and at least a portion of insert 52 are disposed within cavity 24 and cavity 24 includes a substantially void portion 54, as shown in FIGS. 3 and 4. In some embodiments, portion 54 can include one or a plurality of open spaces and/or non-occupied volumes, which may be continuous or non-continuous, uniform or non-uniform, and/or variously configured, such as, for example, those alternatives described herein.

In one embodiment, a portion of insert 52 is disposed within cavity 24 due to disposal of body 32 within cavity 24. In one embodiment, a portion of insert 52 is disposed within cavity 24 due to expansion of insert 52 through opening 50 into cavity 24. In one embodiment, one or all of the components of cage 12 can be expanded and cavity 24 does not include a void portion, for example, such that insert 52 substantially occupies the space of cavity 24.

Spinal implant system 10 includes a bone graft implant, such as, for example, an expandable insert 56, as shown in FIG. 1. In some embodiments, insert 56 is selectively configured and dimensioned for disposal within void portion 54. Insert 56 comprises expandable bone graft material, see, for example, the implants and materials described in commonly owned US Patent Application Publication No. 2008/0091270. For example, in one embodiment, insert 56 is expandable from a first configuration, as shown in FIG. 3, to a second, expanded configuration, as shown in FIG. 4, upon exposure to liquid in vivo. In some embodiments, such liquid includes body fluids of a patient. In some embodiments, insert 56 includes demineralized cancellous bone particles and demineralized cortical bone particles such that insert 56 is expandable upon rehydration in vivo. In some embodiments, insert 56 comprises bone graft, such as, for example, those materials described herein.

In some embodiments, one or a plurality of inserts 56 are selectively disposed based on the number, configuration and/or dimension of the one or plurality of open spaces or non-occupied volumes of portion 54. In some embodiments, insert 56 is expandable in one or both axial directions along axis a, and/or in a transverse direction, including angular orientations and perpendicular relative to axis a. In some embodiments, insert 56 is expandable independent of bodies 14, 32 and/or insert 52.

In some embodiments, as shown in FIGS. 5-15, spinal implant system 10 includes insert 52 and/or insert 56 having various configurations and dimensions. In some embodiments, various configurations of inserts 52, 56 may be used to maintain position of inserts 52, 56 with respect to bodies 14, 32, for example. In some embodiments, the expanded diameter d1, shown in FIGS. 5 and 6, may be used to reduce the risk of undesirable or inadvertent placement, expulsion from bodies 14, 32 and/or loss of inserts 52, 56 during manipulation and insertion of cage 12 and to maintain position of inserts 52, 56 with respect to bodies 14, 32 during in vivo expansion of cage 12. Other complementary designs of the insert/cage interface may be used to maintain position of the inserts with respect to the bodies, including, but not limited to counterbores, keyways, and combinations thereof at one or more locations.

Figure 5:
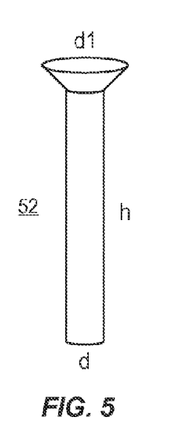
FIGS. 5-15 are perspective views of components of embodiments of a surgical system in accordance with the principles of the present disclosure.
Figure 6:
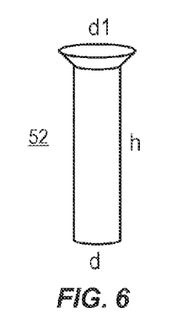

In one embodiment, as shown in FIG. 5, insert 52 includes a cylinder having a height h of 30 mm and a diameter d of 4.3 mm, which extends between a planar end face and a frusto-conical end face having a diameter d1 of 9.2 mm. In one embodiment, as shown in FIG. 6, insert 52 includes a cylinder having a height h of 30 mm and a diameter d of 7.5 mm, which extends between a planar end face and a frusto-conical end face having a diameter d1 of 12.4 mm.

Figure 7:
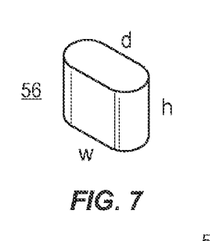
Figure 8:
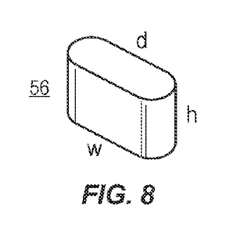
Figure 9:
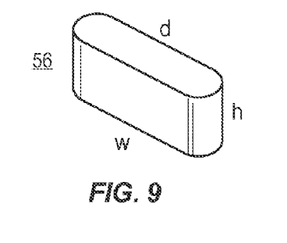

In one embodiment, as shown in FIG. 7, insert 56 includes an oblong, barrel shaped configuration having a width w of 11 mm, a height h of 11 mm, and planar end faces having a depth d of 5.5 mm. In one embodiment, as shown in FIG. 8, insert 56 includes an oblong, barrel shaped configuration having a width w of 15 mm, a height h of 11 mm, and planar end faces having a depth d of 5.5 mm. In one embodiment, as shown in FIG. 9, insert 56 includes an oblong, barrel shaped configuration having a width w of 21 mm, a height h of 11 mm, and planar end faces having a depth d of 5.5 mm.

Figure 10:
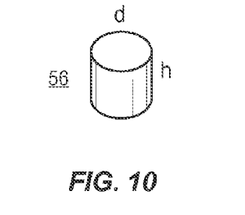
Figure 11:
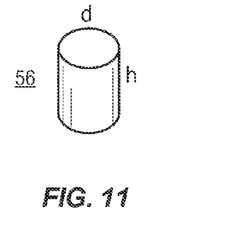

In one embodiment, as shown in FIG. 10, insert 56 includes a cylinder having a height h of 6 mm and extending between planar end faces having a diameter d of 5.2 mm. In one embodiment, as shown in FIG. 11, insert 56 includes a cylinder having a height h of 9 mm and extending between planar end faces having a diameter d of 5.2 mm.

Figure 12:
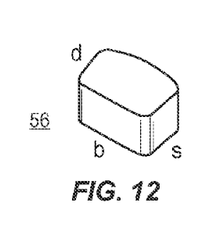
Figure 13:
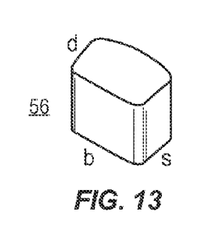
Figure 14:
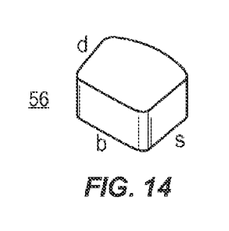
Figure 15:
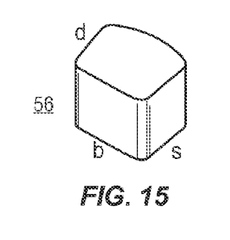

In one embodiment, as shown in FIG. 12, insert 56 includes a three dimensional geometrical shape with three linear sides connected by an arcuate side, which includes an 8 mm base b, 6 mm sides s and a depth d of 6 mm. In one embodiment, as shown in FIG. 13, insert 56 includes a three dimensional geometrical shape with three linear sides connected by an arcuate side, which includes an 8 mm base b, 9 mm sides s and a depth d of 6 mm. In one embodiment, as shown in FIG. 14, insert 56 includes a three dimensional geometrical shape with three linear sides connected by an arcuate side, which includes a 9.5 mm base b, 6 mm sides s and a depth d of 8.5 mm. In one embodiment, as shown in FIG. 15, insert 56 includes a three dimensional geometrical shape with three linear sides connected by an arcuate side, which includes an 9.5 mm base b, 9 mm sides s and a depth d of 8.5 mm.

Referring to FIGS. 16 and 17, in assembly, operation and use, spinal implant system 10 including cage 12 and insert 52 and/or insert 56 disposed therewith, similar to that described with regard to FIGS. 1-15, is employed with a surgical procedure, such as, for example, a lumbar corpectomy for treatment of a spine of a patient including vertebrae V. Spinal implant system 10 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners for securement of cage 12.

Spinal implant system 10 is employed with a lumbar corpectomy including surgical arthrodesis, such as, for example, fusion to immobilize a joint for treatment of an applicable condition or injury of an affected section of a spinal column and adjacent areas within a body. For example, vertebrae V includes a vertebra V1 and a vertebra V2. A diseased and/or damaged vertebra and intervertebral discs are disposed between the vertebrae V1 and V2. In some embodiments, spinal implant system 10 is configured for insertion with a vertebral space to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, corpectomy is performed for treating the spine disorder. The diseased and/or damaged portion of vertebrae V, and diseased and/or damaged intervertebral discs are removed to create a vertebral space S.

A preparation instrument (not shown) is employed to remove disc tissue, fluids, adjacent tissues and/or bone, and scrape and/or remove tissue from endplate surfaces E1 of vertebra V1 and/or endplate surface E2 of vertebra V2. Cage 12 is provided, similar to those described herein, to promote new bone growth and fusion to treat the affected section of vertebrae V.

Cage 12 is disposed in a collapsed configuration, as shown in FIG. 16, for delivery and implantation adjacent a surgical site. Insert 52 is introduced through opening 48 and disposed within cavity 44 and body 32 is disposed within cavity 24. Cage 12 is delivered to the surgical site adjacent vertebrae V with a delivery instrument (not shown) including a driver via the protected passageway for the arthrodesis treatment. The driver delivers cage 12 into the prepared vertebral space S, between vertebra V1 and vertebra V2. Cage 12 is manipulated such that end 18 engages endplate surface E2. A gripping surface, including spikes 19, of end 18 penetrates and fixes with endplate surface E2.

Body 32 is axially translated relative to body 14 for selective expansion in vivo to an expanded configuration, as shown in FIG. 17, and described herein. Bodies 14, 32 are expanded such that body 32 and a portion of insert 52 are disposed within cavity 24 and cavity 24 includes portion 54. As such, cage 12 expands within vertebral space S and end 16 engages endplate surface E1. A gripping surface, including spikes 37, of end 36 penetrates and fixes with endplate surface E1.

In one embodiment, the configuration and dimension of portion 54 is determined, calculated or otherwise selected, which may include factors such as the number of open spaces and/or non-occupied volumes, geometry and size, such that one or a plurality of inserts 56 are selectively configured and dimensioned for disposal within portion 54. Upon such determination, insert(s) 56 is disposed with portion 54. In one embodiment, insert 52 occupies cavity 24 such that no insert 56 is employed. In some embodiments, insert 52 is pre-packed with cage 12 prior to implantation at the surgical site adjacent vertebrae V and insert 56 is post-packed with implanted cage 12 in vivo. In some embodiments, cage 12 is pre-packed insert 52 only such that insert 56 is not post-packed with cage 12. In some embodiments, various combinations of insert(s) 52 and insert(s) 56 may be disposed with cage 12, for example, as described below.

In one example, cage 12 has a mean diameter of 13 mm and is pre-packed with an insert 52, similar those shown in FIGS. 5 and 6. The 13 mm cage can include various alternate height dimensions, for example, a collapsed height of 16 mm that can be expanded to a height of 19 mm, a collapsed height of 19 mm that can be expanded to a height of 23 mm, a collapsed height of 22 mm that can be expanded to a height of 27 mm, a collapsed height of 26 mm that can be expanded to a height of 35 mm, a collapsed height of 32 mm that can be expanded to a height of 46 mm, and a collapsed height of 41 mm that can be expanded to a height of 59 mm. The 13 mm cage is not post-packed with insert 56.

In one example, cage 12 has a mean diameter of 16 mm and is pre-packed with an insert 52, similar those shown in FIGS. 5 and 6. The 16 mm cage can include various alternate height dimensions, for example, a collapsed height of 17 mm that can be expanded to a height of 20 mm, a collapsed height of 20 mm that can be expanded to a height of 25 mm, and a collapsed height of 23 mm that can be expanded to a height of 29 mm. In this example, the 16 mm cage is not post-packed with insert 56.

In one example, cage 12 has a mean diameter of 16 mm, and is pre-packed with an insert 52, similar those shown in FIGS. 5 and 6, and has a collapsed height of 28 mm that can be expanded in a range to a height of 36 mm. In this example, for expansion in a range of 28 mm to 34 mm, the 16 mm cage is not post-packed with insert 56. In this example, for expansion in a range of 35 mm to 36 mm, the 16 mm cage is post-packed with insert 56, as shown in FIG. 10.

In one example, cage 12 has a mean diameter of 16 mm, is pre-packed with an insert 52, similar those shown in FIGS. 5 and 6, and has a collapsed height of 33 mm that can be expanded in a range to a height of 45 mm. In this example, for expansion in a range of 33 mm to 40 mm, the 16 mm cage is not post-packed with insert 56. In this example, for expansion in a range of 41 mm to 45 mm, the 16 mm cage is post-packed with insert 56, as shown in FIG. 10.

In one example, cage 12 has a mean diameter of 16 mm, is pre-packed with an insert 52, similar those shown in FIGS. 5 and 6, and has a collapsed height of 41 mm that can be expanded in a range to a height of 57 mm. In this example, for expansion in a range of 41 mm to 48 mm, the 16 mm cage is not post-packed with insert 56. In this example, for expansion in a range of 49 mm to 52 mm, the 16 mm cage is post-packed with insert 56, as shown in FIG. 10. In this example, for expansion in a range of 53 mm to 57 mm, the 16 mm cage is post-packed with insert 56, as shown in FIG. 11.

In one example, cage 12 has a mean diameter of 19 mm and is pre-packed with an insert 52, similar those shown in FIGS. 5 and 6. The 19 mm cage can include various alternate height dimensions, for example, a collapsed height of 19 mm that can be expanded to a height of 23 mm, and a collapsed height of 23 mm that can be expanded to a height of 29 mm. In this example, the 19 mm cage is not post-packed with insert 56.

In one example, cage 12 has a mean diameter of 19 mm, is pre-packed with an insert 52, similar those shown in FIGS. 5 and 6, and has a collapsed height of 28 mm that can be expanded in a range to a height of 39 mm. In this example, for expansion in a range of 28 mm to 35 mm, the 19 mm cage is not post-packed with insert 56. In this example, for expansion in a range of 36 mm to 39 mm, the 19 mm cage is post-packed with insert 56, as shown in FIG. 14.

In one example, cage 12 has a mean diameter of 19 mm, is pre-packed with an insert 52, similar those shown in FIGS. 5 and 6, and has a collapsed height of 36 mm that can be expanded in a range to a height of 51 mm. In this example, for expansion in a range of 36 mm to 43 mm, the 19 mm cage is not post-packed with insert 56. In this example, for expansion in a range of 44 mm to 51 mm, the 19 mm cage is post-packed with insert 56, as shown in FIG. 14.

In one example, cage 12 has a mean diameter of 19 mm, is pre-packed with an insert 52, similar those shown in FIGS. 5 and 6, and has a collapsed height of 47 mm that can be expanded in a range to a height of 73 mm. In this example, for expansion in a range of 47 mm to 54 mm, the 19 mm cage is not post-packed with insert 56. In this example, for expansion in a range of 55 mm to 61 mm, the 19 mm cage is post-packed with insert 56, as shown in FIG. 14. In this example, for expansion in a range of 62 mm to 68 mm, the 19 mm cage is post-packed with two inserts 56, as shown in FIG. 14. In this example, for expansion in a range of 69 mm to 73 mm, the 19 mm cage is post-packed with three inserts 56, as shown in FIG. 14.

In one example, cage 12 has a mean diameter of 19 mm, is pre-packed with an insert 52, similar those shown in FIGS. 5 and 6, and has a collapsed height of 69 mm that can be expanded in a range to a height of 108 mm. In this example, for expansion in a range of 69 mm to 76 mm, the 19 mm cage is not post-packed with insert 56. In this example, for expansion in a range of 77 mm to 82 mm, the 19 mm cage is post-packed with insert 56, as shown in FIG. 14. In this example, for expansion in a range of 83 mm to 89 mm, the 19 mm cage is post-packed with two inserts 56, as shown in FIG. 14. In this example, for expansion in a range of 90 mm to 96 mm, the 19 mm cage is post-packed with three inserts 56, as shown in FIG. 14. In this example, for expansion in a range of 97 mm to 108 mm, the 19 mm cage is post-packed with two inserts 56, as shown in FIG. 14, and one insert 56, as shown in FIG. 15.

In one example, cage 12 has a mean diameter of 22 mm and is pre-packed with an insert 52, similar those shown in FIGS. 5 and 6. The 22 mm cage can include various alternate height dimensions, for example, a collapsed height of 21 mm that can be expanded to a height of 26 mm, and a collapsed height of 25 mm that can be expanded to a height of 33 mm. In this example, the 22 mm cage is not post-packed with insert 56.

In one example, cage 12 has a mean diameter of 22 mm, is pre-packed with an insert 52, similar those shown in FIGS. 5 and 6, and has a collapsed height of 31 mm that can be expanded in a range to a height of 41 mm. In this example, for expansion in a range of 31 mm to 37 mm, the 22 mm cage is not post-packed with insert 56. In this example, for expansion in a range of 38 mm to 41 mm, the 22 mm cage is post-packed with insert 56, as shown in FIG. 14.

In one example, cage 12 has a mean diameter of 22 mm, is pre-packed with an insert 52, similar those shown in FIGS. 5 and 6, and has a collapsed height of 37 mm that can be expanded in a range to a height of 53 mm. In this example, for expansion in a range of 37 mm to 43 mm, the 22 mm cage is not post-packed with insert 56. In this example, for expansion in a range of 44 mm to 49 mm, the 22 mm cage is post-packed with insert 56, as shown in FIG. 14. In this example, for expansion in a range of 50 mm to 53 mm, the 22 mm cage is post-packed with insert 56, as shown in FIG. 7.

In one example, cage 12 has a mean diameter of 22 mm, is pre-packed with an insert 52, similar those shown in FIGS. 5 and 6, and has a collapsed height of 48 mm that can be expanded in a range to a height of 75 mm. In this example, for expansion in a range of 48 mm to 54 mm, the 22 mm cage is not post-packed with insert 56. In this example, for expansion in a range of 55 mm to 58 mm, the 22 mm cage is post-packed with insert 56, as shown in FIG. 14. In this example, for expansion in a range of 59 mm to 61 mm, the 22 mm cage is post-packed with insert 56, as shown in FIG. 15. In this example, for expansion in a range of 62 mm to 68 mm, the 22 mm cage is post-packed with insert 56, as shown in FIG. 6, and insert 56, as shown in FIG. 14. In this example, for expansion in a range of 69 mm to 75 mm, the 22 mm cage is post-packed with two inserts 56, as shown in FIG. 7.

In one example, cage 12 has a mean diameter of 22 mm, is pre-packed with an insert 52, similar those shown in FIGS. 5 and 6, and has a collapsed height of 68 mm that can be expanded in a range to a height of 107 mm. In this example, for expansion in a range of 68 mm to 75 mm, the 22 mm cage is not post-packed with insert 56. In this example, for expansion in a range of 76 mm to 79 mm, the 22 mm cage is post-packed with insert 56, as shown in FIG. 14. In this example, for expansion in a range of 80 mm to 82 mm, the 22 mm cage is post-packed with insert 56, as shown in FIG. 15. In this example, for expansion in a range of 83 mm to 89 mm, the 22 mm cage is post-packed with insert 56, as shown in FIG. 7, and insert 56, as shown in FIG. 14. In this example, for expansion in a range of 90 mm to 96 mm, the 22 mm cage is post-packed with two inserts 56, as shown in FIG. 7. In this example, for expansion in a range of 97 mm to 107 mm, the 22 mm cage is post-packed with two inserts 56, as shown in FIG. 7, and one insert 56, as shown in FIG. 14.

In one example, cage 12 has a mean diameter of 25 mm and is pre-packed with an insert 52, similar those shown in FIGS. 5 and 6. The 25 mm cage can include various alternate height dimensions, for example, a collapsed height of 21 mm that can be expanded to a height of 26 mm, and a collapsed height of 25 mm that can be expanded to a height of 33 mm. In this example, the 25 mm cage is not post-packed with insert 56.

In one example, cage 12 has a mean diameter of 25 mm, is pre-packed with an insert 52, similar those shown in FIGS. 5 and 6, and has a collapsed height of 31 mm that can be expanded in a range to a height of 41 mm. In this example, for expansion in a range of 31 mm to 38 mm, the 25 mm cage is not post-packed with insert 56. In this example, for expansion in a range of 39 mm to 41 mm, the 25 mm cage is post-packed with insert 56, as shown in FIG. 14.

In one example, cage 12 has a mean diameter of 25 mm, is pre-packed with an insert 52, similar those shown in FIGS. 5 and 6, and has a collapsed height of 37 mm that can be expanded in a range to a height of 53 mm. In this example, for expansion in a range of 37 mm to 44 mm, the 25 mm cage is not post-packed with insert 56. In this example, for expansion in a range of 45 mm to 50 mm, the 25 mm cage is post-packed with insert 56, as shown in FIG. 14. In this example, for expansion in a range of 50 mm to 53 mm, the 25 mm cage is post-packed with two inserts 56, as shown in FIG. 14.

In one example, cage 12 has a mean diameter of 25 mm, is pre-packed with an insert 52, similar those shown in FIGS. 5 and 6, and has a collapsed height of 48 mm that can be expanded in a range to a height of 75 mm. In this example, for expansion in a range of 48 mm to 55 mm, the 25 mm cage is not post-packed with insert 56. In this example, for expansion in a range of 56 mm to 62 mm, the 25 mm cage is post-packed with insert 56, as shown in FIG. 14. In this example, for expansion in a range of 63 mm to 69 mm, the 25 mm cage is post-packed with insert 56, as shown in FIG. 14, and insert 56, as shown in FIG. 15. In this example, for expansion in a range of 70 mm to 75 mm, the 25 mm cage is post-packed with two inserts 56, as shown in FIG. 14, and one insert 56, as shown in FIG. 15.

In one example, cage 12 has a mean diameter of 25 mm, is pre-packed with an insert 52, similar those shown in FIGS. 5 and 6, and has a collapsed height of 68 mm that can be expanded in a range to a height of 107 mm. In this example, for expansion in a range of 68 mm to 75 mm, the 25 mm cage is not post-packed with insert 56. In this example, for expansion in a range of 76 mm to 82 mm, the 25 mm cage is post-packed with insert 56, as shown in FIG. 14. In this example, for expansion in a range of 83 mm to 90 mm, the 25 mm cage is post-packed with insert 56, as shown in FIG. 14, and insert 56, as shown in FIG. 15. In this example, for expansion in a range of 90 mm to 98 mm, the 25 mm cage is post-packed with insert 56, as shown in FIG. 7, and insert 56, as shown in FIG. 14. In this example, for expansion in a range of 99 mm to 107 mm, the 25 mm cage is post-packed with two inserts 56, as shown in FIG. 14, and two inserts 56, as shown in FIG. 15.

Cage 12 engages and spaces apart opposing endplate surfaces E1, E2 and is secured within vertebral space S to stabilize and immobilize portions of vertebrae V in connection with bone growth for fusion and fixation of vertebrae V1, V2. Fixation of implant 20 with endplate surfaces E1, E2 may be facilitated by the resistance provided by the joint space and/or engagement with endplate surfaces E1, E2.

In some embodiments, cage 12 may engage only one endplate. Components of spinal implant system 10 including cage 12 can be delivered or implanted as a pre-assembled device or can be assembled in situ. Components of spinal implant system 10 including cage 12 may be completely or partially revised, removed or replaced in vivo. In some embodiments, one or all of the components of spinal implant system 10 can be delivered to the surgical site via mechanical manipulation and/or a free hand technique.

In one embodiment, cage 12 may include fastening elements, which may include locking structure, configured for fixation with vertebrae V1, V2 to secure joint surfaces and provide complementary stabilization and immobilization to a vertebral region. In some embodiments, locking structure may include fastening elements such as, for example, rods, plates, clips, hooks, adhesives and/or flanges. In some embodiments, spinal implant system 10 can be used with screws to enhance fixation. In some embodiments, spinal implant system 10 and any screws and attachments may be coated with an agent, similar to those described herein, for enhanced bony fixation to a treated area. The components of spinal implant system 10 can be made of radiolucent materials such as polymers. Radiomarkers may be included for identification under x-ray, fluoroscopy, CT or other imaging techniques.

In one embodiment, spinal implant system 10 includes a plurality of cages 12. In some embodiments, employing a plurality of cages 12 can optimize the amount vertebral space S can be spaced apart such that the joint spacing dimension can be preselected. The plurality of cages 12 can be oriented in a side by side engagement, spaced apart and/or staggered.

In some embodiments, the use of microsurgical and image guided technologies may be employed to access, view and repair spinal deterioration or damage, with the aid of spinal implant system 10. Upon completion of the procedure, the non-implanted components, surgical instruments and assemblies of spinal implant system 10 are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
   a first member including a wall that defines a first cavity;
   a second member extending between a first end comprising spikes and a second end, the second member defining a longitudinal axis, the second member including a wall defining a second cavity;
   at least one first expandable bone graft disposable within the second cavity;
   wherein the second end is disposable within the first cavity such that the second member is axially translatable relative to the first member between a first configuration and a second, expanded configuration such that at least a portion of the at least one first graft is disposed within the first cavity and the first cavity includes a substantially void portion; and
   at least one second bone graft having a selective configuration and dimension for disposal within the substantially void portion.

2. A spinal implant as recited in claim 1, wherein the at least one first graft is expandable in at least an axial direction such that the at least one first graft is expandable into the first cavity.

3. A spinal implant as recited in claim 1, wherein the at least one first graft is expandable in at least an axial direction such that the at least one first graft is expandable into the first cavity and a lateral direction.

4. A spinal implant as recited in claim 1, wherein the members are expandable independent of the at least one first graft.

5. A spinal implant as recited in claim 1, wherein the at least one second graft is expandable such that the at least one first graft, the at least one second graft and the members are each independently expandable.

6. A spinal implant as recited in claim 1, wherein the at least one first graft is expandable between a first configuration and a second configuration such that the at least one first graft engages an inner surface of the wall of the second member and the inner surface includes an expansion limit for at least a portion of the expanded at least one first graft.

7. A spinal implant as recited in claim 1, wherein the at least one first graft includes a cylindrical insert being selectively configured and dimensioned for disposal within the second cavity and expansion into the first cavity.

8. A spinal implant as recited in claim 1, wherein the at least one second graft includes an insert having an oblong barrel shaped cross section selectively configured and dimensioned for disposal within the substantially void portion.

9. A spinal implant as recited in claim 1, wherein the at least one second graft includes an insert having a cross section including three straight sides and one curved side selectively configured and dimensioned for disposal within the substantially void portion.

10. A spinal implant as recited in claim 1, wherein the at least one first graft is disposable from a first configuration to a second, expanded configuration upon exposure to liquid in vivo.

11. A spinal implant as recited in claim 1, wherein the at least one first graft includes demineralized cancellous bone particles and demineralized cortical bone particles, the at least one first graft being expandable upon rehydration in vivo.

12. A spinal implant as recited in claim 1, wherein the spikes extend parallel to the longitudinal axis and are configured to engage an endplate surface of a vertebra when the second member is in the second, expanded configuration.

13. A spinal implant comprising:
   an outer body including a wall having an inner surface that defines a chamber;
   an inner body extending between a first end comprising spikes and defining an opening and a second end, the inner body defining a longitudinal axis, the inner body including a wall defining an axial channel;
   at least one cylindrical insert comprising demineralized cancellous bone particles and demineralized cortical bone particles, the at least one insert being selectively configured and dimensioned for disposal within the axial channel and expansion upon exposure to liquid in vivo into the chamber;
   wherein the second end is disposable within the chamber such that the inner body is axially translatable relative to the outer body between a first configuration and a second, expanded configuration such that at least a portion of the at least one insert is disposed within the chamber and the chamber includes a substantially void portion; and
   bone graft having a selective configuration and dimension for disposal within the substantially void portion.

* * * * *